US008672903B2

(12) United States Patent
Hunt et al.

(10) Patent No.: US 8,672,903 B2
(45) Date of Patent: *Mar. 18, 2014

(54) ABDOMINAL WOUND DRESSING

(75) Inventors: Kenneth Hunt, Wimborne (GB); Keith Heaton, Poole (GB); Wayne Schroeder, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 10 days.

This patent is subject to a terminal disclaimer.

(21) Appl. No.: 13/466,917

(22) Filed: May 8, 2012

(65) Prior Publication Data

US 2012/0220963 A1 Aug. 30, 2012

Related U.S. Application Data

(60) Continuation of application No. 13/113,914, filed on May 23, 2011, now Pat. No. 8,187,210, which is a division of application No. 12/127,668, filed on May 27, 2008, now Pat. No. 7,951,100, which is a continuation of application No. 10/275,671, filed as application No. PCT/GB01/02035 on May 9, 2001, now Pat. No. 7,381,859.

(30) Foreign Application Priority Data

May 9, 2000 (GB) .................................. 0011202.9

(51) Int. Cl.
*A61F 5/00* (2006.01)
*A61F 13/00* (2006.01)
*A61M 1/00* (2006.01)
*A61M 35/00* (2006.01)

(52) U.S. Cl.
USPC ................... 604/290; 602/2; 602/41; 602/46; 604/289; 604/313

(58) Field of Classification Search
USPC .............. 602/41–43, 46, 48, 2; 604/304–308, 604/289–292, 313
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 8/1982
AU 745271 4/1999
(Continued)

OTHER PUBLICATIONS

N.A. Bagautdinov, "Variant of External Vacuum Aspiration in the Treatment of Purulent Diseases of the Soft Tissues," Current Problems in Modem Clinical Surgery: Interdepartmental Collection, edited by V. Ye Volkov et al. (Chuvashia State University, Cheboksary, U.S.S.R. 1986);pp. 94-96 (certified translation).

(Continued)

*Primary Examiner* — Kim M Lewis

(57) ABSTRACT

An abdominal wound dressing and methods of use are described that enable the application of negative pressure to the wound site in a healing manner while also limiting the formation of adhesions that would prevent the removal of the dressing. The dressing comprises a layer of porous foam material enclosed by sheets of elastomeric material punctuated by a number of appropriately placed holes. Multiple layers of porous foam may also be used. A suction tube connector is provided on an upper surface of a layer of foam for connection to a negative pressure source. At least one layer of foam is enclosed in elastomeric material and is placed in direct contact with the tissue within the open wound. Fluids are drawn by negative pressure through the holes positioned in the elastomeric envelope and through the foam.

22 Claims, 2 Drawing Sheets

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 8,187,210 B2 * | 5/2012 | Hunt et al. .................. 602/2 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |

FOREIGN PATENT DOCUMENTS

| | | |
|---|---|---|
| AU | 455496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | WO 9742985 A1 * | 11/1997 |
| WO | 99/13793 | 3/1999 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

(56) References Cited

OTHER PUBLICATIONS

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinoviec, V. Đukić, Ž. Maksimović, Đ. . Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

* cited by examiner

ABDOMINAL WOUND DRESSING

CROSS-REFERENCE TO RELATED APPLICATIONS

This application is a continuation of U.S. patent application Ser. No. 13/113,914, filed May 23, 2011, now U.S. Pat No. 8,187,210, which is a divisional of U.S. patent application Ser. No. 12/127,668, filed May 27, 2008, now U.S. Pat. No. 7,951,100, which is a continuation of U.S. patent application Ser. No. 10/275,671, filed Jun. 10, 2003, now U.S. Pat. No. 7,381,859, which was the National Stage of International Application No. PCT/GB01/02035, filed May 9, 2001, which claimed the benefit of Great Britain Application No. 0011202.9, filed May 9, 2000. All of these applications are hereby incorporated by reference.

BACKGROUND OF THE INVENTION

1. Field of the Invention

The invention relates generally to methods and devices used for healing wounds caused by injury or surgery, and more specifically to methods and devices for facilitating the healing of open wounds such as abdominal wounds that benefit from temporary closure and later reopening before final closure.

2. Description of Related Art

Significant advances have been made in preventing post-operative infections. Still, post operative treatment of patients receiving many types of invasive surgeries, especially those involving the abdominal cavity, is enhanced by the ability to re-enter the cavity in order to address peritonitis and other infections that often inhibit the final healing of the wound and the internal organs. While the optimum outcome is no post-operative infections or other complications whatsoever, such complications occur frequently. Their occurrence has lead to the now common practice of establishing a temporary wound closure and, later, re-entering the wound for the purposes of cleansing the abdominal cavity, and for treating such complications, which must be treated before final, or definitive, closure.

The background description in U.S. Pat. No. 5,437,683 issued to Neumann et al., entitled Surgical Closure, the disclosure of which is incorporated herein by reference, reviews various complications associated with abdominal surgery and the process of post-operative cleansing of the abdominal cavity. Neumann et al. teaches a somewhat complex solution to establishing a re-enterable wound closure, namely, a flexible fabric or plate like securing device that covers the wound, provides a suction tube, and extends outward into a larger, sealable tube that may be re-entered as needed before final closure.

Many other techniques for post-operative temporary wall closure after abdominal surgery have been described. Studying these techniques enables the establishment for objective criteria by which to judge the suitability of various proposed temporary closure modalities.

A suitable temporary closure should be simple, easy to apply, effective in containing the abdominal contents, minimally interfere with the abdominal organs and surrounding tissue, minimally, if at all, promote the formation of adhesions and fistula, and promote process towards definitive closure.

A problem common to many existing methods of temporary wound closure is adhesion formation between the tissue and the material in contact with the wound. Such adhesions are undesirable, and complicate the process of preparing the wound site for final closure. Placing porous materials such as gauze, surgical towels and even open cell foam, in direct contact with the open wound site, further complicates final closure by providing increased surface area that promotes adhesion formation, thereby making removal of this material even more difficult.

Maintaining negative pressure on a wound site without creating conditions that make the removal of the temporary wound covering material more difficult, is manifestly beneficial. A desirable layered wound covering permits both the application of negative pressure and the resultant removal of exuded fluids. Such a covering is re-enterable for the purpose of cleansing the wound without trauma to the wound site. Such a wound covering would be most advantageous for open abdomen surgical wounds. These devices and techniques could also be used on other types of open wounds that present a difficult healing process.

The need for a wound covering, and therapeutic treatment system that allows the application of therapeutic negative pressure without causing increased adverse side effects to the open wound site is apparent. Presently, no such wound covering, or treatment system is known to exist. It is towards the filling of this need that the present invention is directed.

SUMMARY

An object of the present invention is to provide a layered wound dressing that serves as a temporary covering for an open wound and permits the application of negative pressure for the removal of exuded fluids from the wound.

A further object of the present invention to provide a wound dressing that permits the application of negative pressure for the removal of fluids from the wound site in a manner that facilitates the healing of the wound, and minimizes adhesion formation between the wound dressing and the underlying tissue.

Another object of the present invention to provide a wound dressing that permits the application of negative pressure for the removal of fluids from the wound site in a manner that does not promote the formation of adhesions between the wound dressing and the underlying tissue and yet provides a porous medium through which the exuded fluids may pass without experiencing excessive blockage that would degrade the effectiveness of the negative pressure.

A still further object of the present invention to provide an abdominal wound dressing that serves as a temporary covering for an open abdominal wound and permits the application of negative pressure for the removal of exuded fluids from the wound while being easily retracted from the wound site for the purpose of permitting repeated access to the abdominal cavity for cleansing and/or treatment.

In fulfillment of these and other objectives the present invention provides an abdominal wound dressing and methods for its use that permit the application of negative pressure to the wound site in a manner that promotes the healing of the site while limiting the formation of adhesions that would prevent the removal of the dressing.

According to one aspect of the present invention there is provided a removable wound closure which comprises a porous pad which is permeable to liquids for placement on or in a wound, the porous pad comprising a polymer foam having interconnecting cells and a sheet of flexible plastics film having a plurality of holes in its surface, the plastics film being in contact with a surface of the porous pad so that in use, the plastics film is disposed between the surface of the wound and the pad, a film drape which is impermeable to liquids for placement over the porous pad, the film drape having an adhesive perimeter for sealing to an area of skin surrounding the wound and connection means extending through the film drape and in flow communication with the porous pad for connection to a source of negative pressure for stimulating a flow of exuded liquids from the wound.

The holes in the flexible plastics film should constitute a sufficiently small proportion of the area of the film in contact with the wound so that there is limited ingrowth of fibrous tissue into the sheet. In this way, the film does not become adhered to the wound but remains relatively easy to remove. Preferably, the holes in the film should constitute less than 10%, especially less than 5% or even 1 to 2% or less of the effective area of the film. Openings in the form of slits or slots are preferred because these constitute a very small proportion of the area of the film.

The slits or slots may typically be 0.5 to 2 cms, e.g. 1 to 1.5 cm in length and may be aligned in rows and separated by 10 to 40 mil spaces, e.g. 20 to 30 mil spaces.

The flexible film should be sufficiently stiff to hold its shape. A suitable material is plasticised pvc of 30 to 80 microns in thickness, e.g. 40 to 60 microns.

In use, the film is trimmed to size such that it overlaps the wound edge. An absorbent polymer foam, e.g. a reticulated polyurethane foam, is trimmed to size so that it fits within the boundary of the wound. The trimmed foam pad is placed on the cut film so that the edges of the film extend beyond the perimeter of the foam, e.g. by abaout 20 to 80 mm, preferably 40 to 60 mm, typically about 50 mm. A surgical drape of elastomeric film-like material is placed over the foam pad and the flexible plastics film so as to encapsulate and provide an air-tight seal over the wound dressing. A suction tube or connector is arranged to extend through the surgical drape into the polymer foam or into close proximity with it. The suction tube or connector is sealed to the surgical drape so that the space beneath the drape can be maintained at a pressure below atmospheric by connecting the suction tube or connector to a source of negative pressure. A preferred suction tube connector head is described in GB Patent No. 2329127 and in U.S. Pat. No. 6,216,701, the disclosure of which is specifically incorporated herein by reference.

Surgical drapes conventionally comprise a thin elastomeric film which is coated overall on one side with a tacky, pressure-sensitive adhesive. Usually, a protective sheet which is treated with a release agent contacts the adhesive surface and is stripped away just before use to reveal the adhesive surface. For the purposes of this invention, the assembly of the adhesive elastomeric film and protective film are cut to size (and if appropriate, a hole cut for the suction tube or connector) prior to stripping away the protective sheet.

Suitable elastomeric films include polyurethane and polybutadiene. Commerically available surgical drapes include those marketed by the 3M Company under the trade mark "Tegaderm".

The foam may comprise multiple layers. A suction tube spigot or connector is provided on the upper surface of foam for connection to a negative pressure source. Instead of employing a flexible plastics sheet in contact with the wound and a separate portion of polymer foam, the foam may be enclosed in an envelope of plastics film. In this embodiment, the plastics film may be elastomeric in nature and the film need not extend beyond the perimeter of the foam. However, it is convenient to provide a flange of film extending beyond the perimeter of the foam, e.g. by about 20 to 80 mm, more usually about 40 to 60 mm, typically about 50 mm. Suitable elastomeric film materials include polyurethane (PTFE), or polybutadiene films, similar to those used for surgical drapes. Preferably, the elastomeric film has a thickness of about 30 to 70 microns, especially 40 to 60 microns, typically about 50 microns. A number of differently sized polymer foam slabs will be cut, shaped and enclosed in an envelope of elastomeric film material. It may be convenient to weld the film to form the envelope using ultrasonic or heat welding. Commonly, abdominal wounds are approximately elliptical in shape and the foam pad is also preferably elliptical in shape. Typical sizes for the foam pads may be about 280, 320 and 380 mm for the major dimension and about 140, 175 and 250 mm for the minor dimension. A polyurethane foam having a thickness of about 5 to 10 mm, e.g. about 6 mm, is suitable. Polyurethane foams having a pore size of about 30 to 50, e.g. 40 pores per inch are preferred. Polyether foams or polyvinyl alcohol foams may alternatively be used. If multiple layers of foam are employed, different foams may be used in different layers. For example, the layer in contact with the lower film may be of polyvinyl alcohol foam and the upper foam layer(s) may be of polyurethane.

In the multi-layer embodiment, at least one lower layer of foam may be enclosed in elastomeric material and placed in direct contact with the tissue within the open wound. In another embodiment, only a single layer of foam is used, and the envelope of elastomeric material containing the layer of foam is placed in direct contact with the open wound.

Fluids are drawn by negative pressure through the holes in the flexible or elastomeric material, and then through the foam. In the multi layer embodiment, fluids are drawn by negative pressure through the holes located in the elastomeric envelope, through the lower layer(s) of foam, again through holes in the elastomeric envelope, and then through the upper layer of foam that is placed over the enveloped lower layer(s).

In the multi layer embodiment, the lower layer(s) of foam may be of a finer porosity while the upper layer of foam may be coarser. In all embodiments of the present invention, an adhesive elastomeric sheet, e.g. a surgical drape, covers the entire wound dressing and seals the edges to the skin surrounding the wound. An appropriate vacuum device is attached to the suction tube spigot or connector to provide therapeutic negative pressure.

DETAILED DESCRIPTION OF THE PRESENT INVENTION

The present invention lends itself to use in conjunction with surgical techniques that require repeated access to the abdominal cavity after surgery therein. The present invention is directed toward providing a removable and beneficial dressing that facilitates both healing of the wound and its final closure.

Reference is made to U.S. patent application Ser. No. 08/951,832 and also to U.S. Ser. No. 09/078,223 and GB Patent No. 2307180 (WO 94/20041 and WO 97/18007), for a description of a negative pressure system suitable for implementing the vacuum required for use of the dressing structures, and treatment method, described herein. The disclosure of these documents is incorporated herein by reference. Negative pressure is defined herein as a vacuum of less than 1 atmosphere of pressure. Controlling the negative pressure and collecting and disposing of exuded fluids are also described in the above cited references. The manner of using such systems in conjunction with the dressing structure described herein will become apparent to those of ordinary skill in the art.

Figure 1:
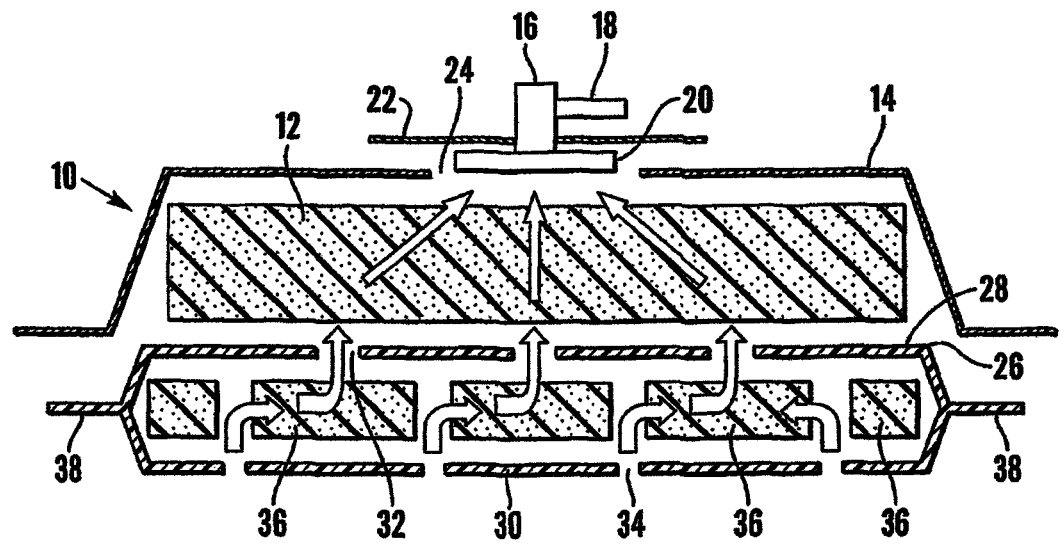
FIG. 1 is a cross sectional view of the device of a first embodiment of the present invention showing the use of a combination single foam layer within an envelope and an overlay of a second foam layer.
Figure 2:
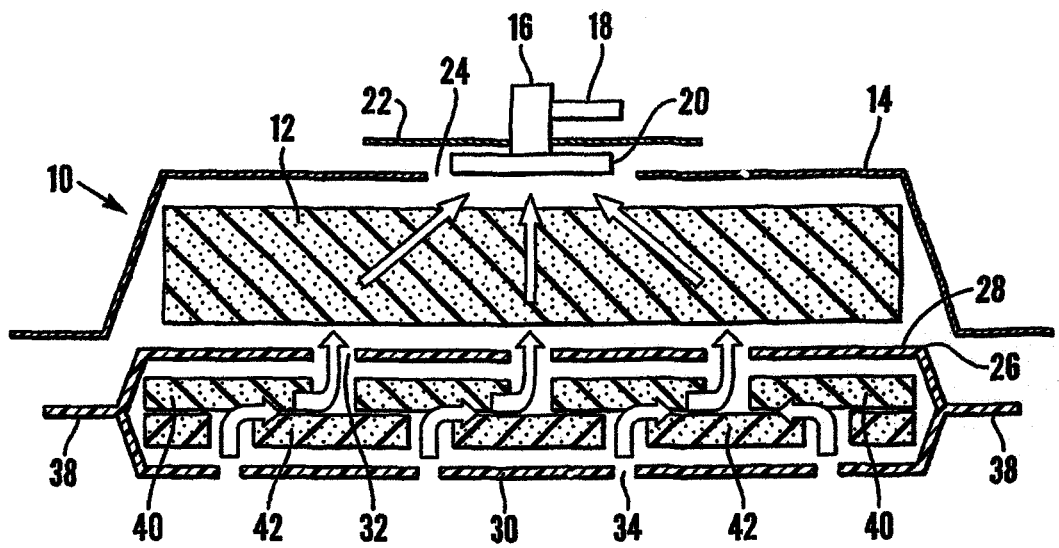
FIG. 2 is a cross sectional view of a second embodiment of the present invention similar to FIG. 1 but showing the use of a double foam layer within an envelope.

Reference is made to FIG. 1 for a description of a first embodiment of the present invention wherein a single lower layer of foam is utilized in the wound contact layer of the dressing. Both FIG. 1 and FIG. 2 are partially exploded views of the dressing of the present invention. During use, the layers of foam and the intervening sheets of elastomeric material would be in close and sometimes sealed contact with each other.

The complete wound dressing 10 shown in FIG. 1 comprises upper foam layer 12 and lower foam layer 36. Lower foam layer 36 is enveloped within two sheets of elastomeric material 38 such as are used for the membranes of surgical drapes. The elastomeric sheets 38 may preferably be constructed from polyurethane film, which provides both the necessary strength and resiliency needed for placement in direct contact with the wound. Another suitable material is polytetrafluoroethylene (PTFE). Elastomeric sheets 38 are sealed on their periphery, e.g. by welding or adhesive, in a manner that surrounds the lower layer of foam 36 to form a lower layer envelope 26. Elastomeric sheets 38 resist the formation of wound adhesions and are therefore appropriate for placement in direct contact with the tissue surfaces within the wound and around the wound periphery.

Placing such non-porous film material in contact with the wound opening, rather than open cell foam or a mesh material greatly reduces the occurrence of adhesions that, over time would make removal of the dressing difficult or dangerous. The pliable and flexible lower layer envelope 26 is easily inserted over and/or into the wound. The lower layer envelope 26 may, as desired, be placed either over the wound wherein the edges of the layer are in contact with the skin surrounding the wound or preferably into the wound leaving the upper surface of the upper surface of the lower layer envelope exposed above the wound.

Figure 3:
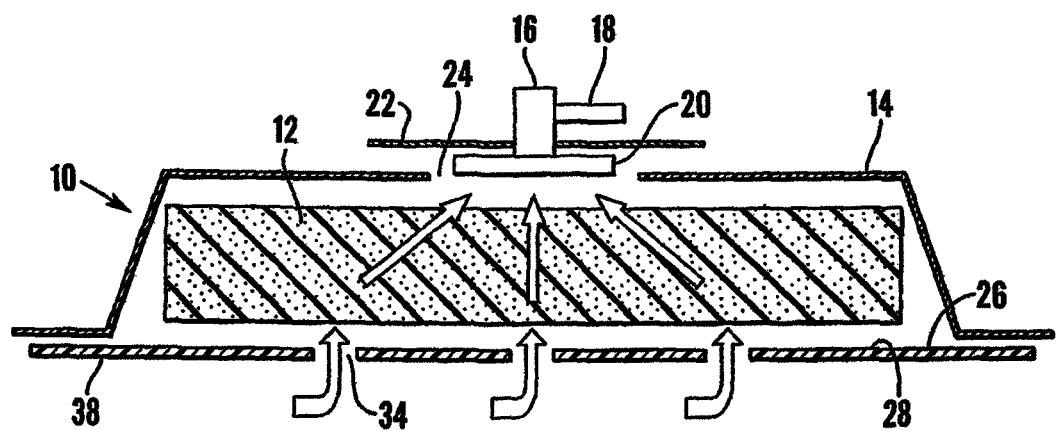
FIG. 3 is a third embodiment comprising a flexible sheet and a layer of foam thereon.

The overall dressing 10 has a generally flat profile as shown in cross section in FIG. 2 and FIG. 3. The shape of the dressing can vary significantly depending on the size and shape of the wound to which it is to be applied. A rectangular or square shape having dimensions on the order of 8 inches by 8 inches up to as much as 18 inches by 18 inches might be appropriate for use in conjunction with the abdominal wounds described above. Other dimensions and shapes, such as circular, oval or even oblong may be suitable for other types of wounds. Typical dimensions for thicknesses and for planar dimensions of oval or elliptical foam slabs are given above. This basic structure may be easily implemented with any of these, or even other, shapes and sizes.

Elastomeric sheets 38 are provided with a plurality of holes 32 and 34 in the upper and lower walls 28 and 30 of the envelope 26 they define. These holes may be of the order of 3 mm (⅛ inch) to 6 mm (¼ inch) in length, diameter or maximum dimension and may be dispersed across the surface of the defined envelope on 25 to 75 mm (1 inch to 3 inch) centres. Preferably, the holes are slit- or slot-shaped. The positions of the holes may be associated with holes positioned into and through lower foam layer 36 as described in more detail below. Where holes are provided in the foam, they may be of different sizes and shapes.

Lower foam layer 36 is preferably constructed from polyurethane having a high degree of reticulation and good permeability under suction. Foams having at least 90% and preferably 95% of interconnecting cells are preferred. Preferably, the foams have from 20 to 60 pores per inch. Preferably, the polyurethane foams are prepared by reacting a hydrophilic polyether polyol with a tolylene diisocyanate in the presence of water. Carbon dioxide is liberated in the reaction which provides a gaseous blowing agent. Pore size can be controlled by temperature and stirring. Reticulation is enhanced by maintaining the foam in the chamber in which the foam is initially formed and causing the blowing agent to expand further and rupturing cell walls.

As indicated above, lower foam layer 36 is punctuated by a plurality of holes that pass entirely though the layer from its upper to lower surface. As will be seen from their placement with respect to holes 32 and 34 in the elastomeric envelope, the holes in the lower foam layer 36 are provided to form "sinks" into which the exuded fluids from the wound may be drawn. Holes 34 in the lower surface of the elastomeric envelope 38 may be positioned directly over the holes in the foam layer 36.

Holes 32 in the upper wall 28 of the elastomeric envelope 26 are preferably positioned so that they are not aligned with the holes in the foam layer 36 and the holes in the lower wall 30 of the envelope 26. In this manner, fluids are withdrawn (by appropriate negative pressure) from the wound into the holes 34 positioned in the lower wall 30 of the envelope 26 and into the "sink" holes in the lower foam layer 36. The fluids are then drawn into the cells of the lower foam layer 36 where they are dispersed before again being drawn through holes in the elastomeric envelope 38, this time in the upper wall 28 of the envelope 26. Placement of the lower foam layer/envelope onto or into the wound therefore requires proper orientation of the holes as shown.

A problem encountered in the prior art has been the deterioration of flow caused by the clogging of the medium through which the exuded fluids, and the accompanying debris, must flow. Such flows are drawn towards the source of the negative pressure thus becoming clogged most quickly along the direct path towards the vacuum source, in this case the suction tube. The present invention disperses the vacuum so as to de-localize the flow. The layers of foam and the spaced holes in the elastomeric sheets provide this dispersion. Even without an interleaved layer of foam, the off set holes accomplish this purpose. The dark arrows in both FIG. 1 and FIG. 2 show the flow of exuded fluid through the dressing.

Upper foam layer 12 provides the initial mechanism for dispersing the vacuum that draws the fluids up from the wound. In the presently preferred embodiment as shown in FIG. 1, upper foam layer 12 is a coarser polyester-based or polyurethane foam having greater rigidity than the lower layer of polyurethane foam. For example, the lower layer of foam 36 may have about 1.5 to 2 times the pores per inch of the coarser foam layer. Typically, the coarse layer of foam may have 20 to 30 pores per inch. Upper foam layer 12 should be somewhat less pliable so as to hold its shape under the influence of even relatively strong negative pressure. Upper foam layer 12 is placed in direct contact with the upper wall 28 of the elastomeric envelope 26 containing lower foam layer 36. Covering upper foam layer 12 and the balance of the dressing is elastomeric drape 14, which in the preferred embodiment is made of the same type of polyurethane film, as is elastomeric envelope 26.

Drape 14 is a single sheet, cut large enough to fully cover upper foam layer 12 and an additional area of skin surrounding the wound site. A pressure sensitive adhesive, such as a permanently tacky acrylic adhesive, is coated on at least the periphery of drape 14 for creating an airtight seal against the skin, effectively closing the dressing and the wound beneath it.

Connector 16 is positioned over a hole 24 cut in drape 14 and is fixed thereto by sealing patch 22. Sealing patch 22, which is circular in the preferred embodiment, adheres to a bottom flange portion 20 of connector 16 as well as drape 14. In this manner, a negative pressure is drawn in upper foam layer 12 when an appropriate suction line is attached to tube connector 18 positioned on connector 16. Flange portion 20 may have a lower surface shaped with channels to direct flow of fluid from the porous pad to the tubular portion 18 of the connector. A suitable suction head connector is shown in GB 2329127 and in U.S. Pat. No. 6,216,701 (WO 99/13793).

Another embodiment of the present invention is depicted in FIG. 3. In this embodiment, the principles of operation are identical, but the dressing is comprised of but a single foam layer, the foam layer within the non-porous film is dispensed with. The foam utilized is black coloured open cell polyurethane currently commercialised in assignee's V.A.C. product.

Referring to FIG. 3, a flexible sheet 38 of semi-stiff plastics material, e.g. formed from plasticized pvc is placed in contact with the wound so that the trimmed edges line the walls of the wound. The sheet is formed with holes 34 which are preferably slits or narrow slots. A reticulated plastics foam is placed on top of the sheet 38. A suction head connector 16 is placed with its flange portion 20 in contact with the top surface of the foam pad and a surgical drape 14 is placed over the foam and the sheet 38 to seal the dressing in the wound.

Instead of providing a separate sealing patch 22 to seal the connector to the dressing, the patch may be part of the surgical drape, as described and illustrated in GB 2,329,127 and U.S. Pat. No. 6,216,701.

The dressing structure of the present invention could be applied in a number of circumstances in association with a variety of different wound types. In the case of an open abdominal wound as might result from surgery, the lower foam layer contained within the elastomeric envelope would be positioned within the wound with the periphery possibly extending under the fascia and peritoneum of the abdominal wall. The upper foam layer could then be cut to a size appropriate for positioning on the exposed upper surface of the lower layer envelope. The drape with the appropriately positioned spigot may then be placed over the upper foam layer and the wound as a whole, extending two or more inches over the skin surrounding the wound, and adhesively holding the dressing in place. Application of a suction line as described above draws the entire dressing onto the wound and serves to initiate the flow of effluent through the dressing.

The thickness of the upper and lower foam layers is determined in part by the desire to have a flat profile to the dressing when it is in place. The more rigid upper layer of foam may, in the preferred embodiment, have a thickness on the order of 25 to 75 mm (1 inch to –3 inches) uncompressed. Its rigidity should limit compression to 80%-90% under the negative pressures normally associated with wound suction and the like. The more pliable lower foam layer, where employed, should have a thickness on the order of 5 to 15 mm, e.g. 5 to 10 mm (about ¼ to ¾ inch) so as to be capable of being easily inserted into the wound.

The structure of the present invention may likewise be utilized on the surface of the skin when the open wound is not associated with an internal cavity or the like. In such a case the periphery of the elastomeric lower envelope may contact the skin surrounding the wound. This is appropriate as long as the periphery of the drape covering the upper foam layer extends suitably beyond the lower envelope to adhere to the skin and seal the dressing. It therefore becomes apparent that the lower elastomeric envelope may be pre-made in a variety of shapes and sizes while the upper foam layer and the drape may be cut, at the time the dressing is placed on the wound, to the appropriate size and configuration.

FIG. 2 discloses an alternate preferred embodiment of the present invention wherein the single lower layer of foam shown in FIG. 1 is replaced with a double layer of foam. In this embodiment, elastomeric envelope 26 encloses a first lower foam layer 40 and a second lower foam layer 42. The advantage realized by this arrangement lies in the offset positioning of the holes interspersed in both foam layers. Holes 34 punctuating the lower wall 30 of elastomeric envelope 26 remain positioned in line with the "sink" holes positioned in the second (bottom) layer of foam 42. Holes 32 punctuating the upper wall 28 of elastomeric envelope 26 are, as described above, offset from alignment with holes 34 in the lower surface of the envelope, but are aligned with the "sink" holes positioned in the first (top) layer of foam 40. Under this structure further dispersion of the flow of fluid occurs thus decreasing the localization of clogging debris and prolonging the effective life of the dressing. The remaining components, applications, and methods of use of the dressing are as described above in conjunction with FIG. 1.

The present invention has been described in conjunction with certain preferred embodiments. Alternative embodiments and further applications of the invention will be anticipated by those skilled in the art without departure from the basic concepts and principles of the invention. Certain materials have been described as suitable for the specific layers of foam and film although a variety of similar materials would be equally suitable. Certain geometries and dimensions have been described as appropriate under various conditions and with various applications of the dressing, especially in conjunction with open and re-enterable abdominal wounds. These geometries and dimensions are not intended as limiting but are described as representative of the various shapes and sizes possible using the fundamental layered structure of the dressing. The scope of the invention is therefore not limited by the foregoing description but is best defined by the specific claims that follow.

We claim:

1. A method for treating a patient, said method comprising:
positioning an envelope member having a plurality of holes formed on the envelope member within a cavity of the patient, the envelope member having a foam material having a plurality of sink holes encompassed within an interior space of the envelope member;
sealing the envelope member within the cavity with a drape positioned in contact with an area of skin surrounding the cavity; and
providing a negative pressure to a sealed space beneath the drape for drawing fluids from the cavity.

2. The method according to claim 1, further comprising sizing the drape to be capable of contacting the area of skin surrounding the cavity prior to positioning the drape in contact with the area of skin surrounding the cavity.

3. A dressing for removing fluid from a wound when subjected to a negative pressure, the dressing comprising:
an envelope member enclosing an interior space and having a wound-facing side comprising an adhesion-resistant film for contacting the wound and a second side for receiving a negative pressure, both the patient-facing side and the second side including a plurality of holes;

a foam material disposed within the interior space of the envelope member and including a plurality of sink holes; and wherein the holes in the patient-facing side and the second side and the sink holes provide a path for removing fluids absorbed from a wound through the foam material.

4. The dressing of claim 3, wherein the holes in the second side are offset from the holes in the patient-facing side.

5. The dressing of claim 3, wherein the holes in the second side are aligned with the holes in the patient-facing side.

6. The dressing of claim 3, further comprising a porous pad disposed over the second side.

7. The dressing of claim 3, wherein the plurality of sink holes are aligned with the holes in the patient-facing side.

8. The dressing of claim 3, wherein the plurality of sink holes are aligned with the holes in the patient-facing side and are offset from the holes in the second side.

9. The dressing of claim 3, wherein the plurality of sink holes are offset from the holes in the patient-facing side.

10. The dressing of claim 3, wherein the plurality of sink holes are offset from the holes in the patient-facing side and are aligned with the holes in the second side.

11. The dressing of claim 3, wherein the foam material comprises a first foam layer and a second foam layer, wherein the first foam layer has a first plurality of sink holes and the second foam layer has a second plurality of sink holes, and wherein the first plurality of sink holes are aligned with the second plurality of sink holes.

12. The dressing of claim 3, wherein the foam material comprises a first foam layer and a second foam layer, wherein the first foam layer has a first plurality of sink holes and the second foam layer has a second plurality of sink holes, and wherein the first plurality of sink holes are offset from the second plurality of sink holes.

13. The dressing of claim 3, further comprising a suction line fluidly coupled to the tubular portion.

14. The dressing of claim 3, wherein the foam material has a rectangular cross section.

15. The dressing of claim 3, wherein the foam material includes a plurality of cells.

16. The dressing of claim 3, wherein the foam material includes a plurality of cells, and further comprising a source of negative pressure in flow communication with the suction line.

17. The dressing of claim 3, wherein the plurality of holes is a plurality of slits.

18. The dressing of claim 3, wherein the envelope member comprises polyurethane.

19. The dressing of claim 3, further comprising a drape disposed over the second side.

20. The dressing of claim 3, further comprising a drape disposed over the second side; and a tube connector positioned through the drape.

21. The dressing of claim 3, further comprising a drape disposed over the second side; and a porous pad disposed between the drape and the second side.

22. The dressing of claim 3, further comprising a drape disposed over the second side; a porous pad disposed between the drape and the second side; and wherein the porous pad is more rigid than the foam material.

\* \* \* \* \*